(12) United States Patent
Hertz et al.

(10) Patent No.: US 9,999,715 B2
(45) Date of Patent: Jun. 19, 2018

(54) BLOOD TREATMENT APPARATUS ADAPTED TO PRESERVE PARTS THEREOF

(75) Inventors: Thomas Hertz, Lund (SE); Mattias Holmer, Lund (SE); Lennart Jonsson, Bjarred (SE); Anders Wieslander, Lund (SE); Helena Jeppsson, Horby (SE)

(73) Assignee: GAMBRO LUNDIA AB, Lund (SE)

( * ) Notice: Subject to any disclaimer, the term of this patent is extended or adjusted under 35 U.S.C. 154(b) by 876 days.

(21) Appl. No.: 14/122,474

(22) PCT Filed: May 23, 2012

(86) PCT No.: PCT/EP2012/059520
§ 371 (c)(1),
(2), (4) Date: Mar. 28, 2014

(87) PCT Pub. No.: WO2012/163737
PCT Pub. Date: Dec. 6, 2012

(65) Prior Publication Data
US 2014/0248600 A1 Sep. 4, 2014

Related U.S. Application Data

(60) Provisional application No. 61/490,633, filed on May 27, 2011.

(30) Foreign Application Priority Data

May 27, 2011 (SE) .................................. 1150493-3

(51) Int. Cl.
*A61M 1/14* (2006.01)
*A61M 1/36* (2006.01)
*A61M 1/16* (2006.01)

(52) U.S. Cl.
CPC .............. *A61M 1/14* (2013.01); *A61M 1/168* (2013.01); *A61M 1/169* (2013.01);
(Continued)

(58) Field of Classification Search
CPC ...... A61M 1/14; A61M 1/168; A61M 1/3643; A61M 1/3649
See application file for complete search history.

(56) References Cited

U.S. PATENT DOCUMENTS

| | | |
|---|---|---|
| 4,431,560 A | 2/1984 | Lake et al. |
| 4,552,721 A | 11/1985 | Fentress et al. |

(Continued)

FOREIGN PATENT DOCUMENTS

| | | |
|---|---|---|
| CN | 101622021 | 1/2010 |
| CN | 101678161 | 3/2010 |

(Continued)

OTHER PUBLICATIONS

Sam Ramin et al., "Composition and Clinical Use of Hemodialysates", Hemodialysis International, vol. 10, No. 1, Jan. 1, 2006 ( pp. 15-28.)

(Continued)

*Primary Examiner* — Tatyana Zalukaeva
*Assistant Examiner* — Kai Weng
(74) *Attorney, Agent, or Firm* — K&L Gates LLP (57) ABSTRACT

A blood treatment apparatus adapted to preserve a blood treatment unit between blood treatment sessions. The blood treatment apparatus is configured to i) perform a blood treatment session and thereby use the blood treatment unit, ii) fill the blood treatment unit with a preservation fluid comprising at least one treatment fluid concentrate of a type that is used to prepare the treatment fluid, iii) maintain the preservation fluid in the blood treatment unit until a next blood treatment session is prepared, iv) dispatch the pres- (Continued)

ervation fluid from the blood treatment unit in preparation of a next blood treatment session, and v) perform a next blood treatment session and thereby extend the use of the blood treatment unit. A related method is also described.

18 Claims, 6 Drawing Sheets

(52) U.S. Cl.
CPC ........ *A61M 1/1682* (2014.02); *A61M 1/1684* (2014.02); *A61M 1/3643* (2013.01); *A61M 1/3644* (2014.02); *A61M 1/3649* (2014.02)

(56) References Cited

U.S. PATENT DOCUMENTS

| | | |
|---|---|---|
| 4,673,506 A | 6/1987 | Henne et al. |
| 4,707,335 A | 11/1987 | Fentress et al. |
| 5,698,100 A | 12/1997 | Levin et al. |
| 5,863,421 A | 1/1999 | Peter, Jr. et al. |
| 5,951,859 A | 9/1999 | Miura et al. |
| 6,022,512 A | 2/2000 | Tanka et al. |
| 6,146,536 A | 11/2000 | Twardowski |
| 6,468,472 B1 | 10/2002 | Yu et al. |
| 8,529,487 B2 | 9/2013 | Fava et al. |
| 8,671,996 B2 | 3/2014 | Weilhoefer et al. |
| 2003/0100858 A1 | 5/2003 | Utterberg et al. |
| 2005/0040110 A1 | 2/2005 | Felding |
| 2009/0004053 A1 | 1/2009 | Kenley |
| 2010/0116740 A1 | 5/2010 | Fulkerson et al. |

FOREIGN PATENT DOCUMENTS

| | | |
|---|---|---|
| WO | 96/40317 A1 | 12/1996 |
| WO | 01/02035 A1 | 1/2001 |
| WO | 2010/042666 A2 | 4/2010 |

OTHER PUBLICATIONS

International Search Report cited in PCT/EP2012/059520 dated Sep. 21, 2012.
European Office Action dated Sep. 2, 2016 in corresponding European application No. 12722160.4 (4 pages).

BLOOD TREATMENT APPARATUS
ADAPTED TO PRESERVE PARTS THEREOF

CROSS RELATED APPLICATION

This application is the U.S. national phase of International Application No. PCT/EP2012/059520 filed 23 May 2012 which designated the U.S. and claims priority to Swedish Patent Application No. 1150493-3 filed 27 May 2011 and U.S. Provisional Patent Application No. 61/490,633 filed 27 May 2011, the entire contents these applications are incorporated by reference.

TECHNICAL FIELD

The present invention generally relates to a blood treatment apparatus and methods for preserving parts of the blood treatment apparatus.

BACKGROUND

Today blood treatment apparatuses are used for extracorporeal blood treatment which involves withdrawing blood from a patient, treating the blood and returning the treated blood to the patient. For this purpose an extracorporeal blood flow circuit (blood line) is used which is connected to a blood vessel access of the patient, typically via one or more access devices such as needles or catheters inserted into a blood vessel of the patient. Depending on method of blood treatment, the blood may be withdrawn from the patient, passed through a blood treatment unit (e.g. dialyzer) and returned to the patient via the same or another blood vessel access device. Simultaneously a fluid line withdraws a treatment fluid (i.e. fresh dialysis fluid) from a fluid source, passes the treatment fluid through the blood treatment unit where the blood is treated, and disposes used/spent treatment fluid to a drain. Extracorporeal blood treatment includes hemodialysis, hemodiafiltration, hemofiltration etc.

During blood treatment it is important that a patient is not exposed to harmful microorganisms. For this reason, new and sterile blood treatment units and bloodlines are typically used for each blood treatment session. Non-disposable parts, such as the fluid line, are typically disinfected on a regular basis to prevent microbial growth therein. Parts in contact with blood, such as the blood line and the blood treatment unit, are usually replaced with new ones when a new patient shall be treated but in some cases, the blood treatment unit and the blood line may be reused for treatment of the same patient at a later time.

Such extended use requires cleaning and disinfection of blood-contacting parts between blood treatment sessions. A number of techniques have been developed for this purpose, which typically include use of cleaning fluids, UV-radiation and/or heat for removing or killing any harmful microorganism.

A well-known cleaning solution is Renalin®, which has been used for blood treatment unit reuse for decades. It is however very harmful, and care must be taken that all Renalin® is rinsed out of the blood treatment unit before it may be used again.

One example of a cleaning technique is disclosed in U.S. Pat. No. 6,146,536 where a hemodialyzer apparatus comprises a reusable dialyzer membrane as well as reusable blood flow path and dialysis flow path units. The apparatus automatically primes itself and makes dialysis solution from dry chemicals, concentrates, and fresh water which is provided to the apparatus. After use, the apparatus automatically prepares a cleaning and rinsing solution for the cleaning and rinsing of the dialyzer membrane as well as the dialyzate and blood flow path means.

Another example of cleaning technique is given by U.S. Pat. No. 6,022,512 disclosing a cleaning and disinfecting method for treating the surfaces of hemodialysis equipment that are exposed to a dialysate or purified water. The method comprises the use of electrolyzed hyperacidity water for cleaning and disinfection.

Known techniques are generally capable of cleaning a blood line or a fluid line of a blood treatment apparatus such that various components may be reused. However, it is believed that present cleaning techniques may be improved in the sense that required hardware components and/or use of cleaning solutions may be reduced, while still safeguarding a patient from harmful microorganisms and toxic substances and allowing extended use of components.

SUMMARY

It is an object of the invention to at least partly overcome one or more limitations of the prior art. In particular, it is an object to provide a blood treatment apparatus that allows efficient extended use of one or more components while still safeguarding a patient from harmful microorganisms.

Hence a blood treatment apparatus is provided which is adapted to preserve a blood treatment unit between blood treatment sessions. The blood treatment apparatus comprises the blood treatment unit, a blood line configured to pass blood through the blood treatment unit and deliver treated blood to a target vessel, and a fluid line configured to pass treatment fluid through the blood treatment unit and deliver used/spent treatment fluid to a drain. The blood treatment apparatus is configured to: i) perform a blood treatment session and thereby use the blood treatment unit, ii) fill the blood treatment unit with a preservation fluid comprising at least one treatment fluid concentrate of a type that is used to prepare the treatment fluid, iii) maintain the preservation fluid in the blood treatment unit until a next blood treatment session is prepared, iv) dispatch the preservation fluid from the blood treatment unit in preparation of a next blood treatment session, and v) perform a next blood treatment session and thereby extend the use of the blood treatment unit.

The blood treatment apparatus is advantageous in that growth of harmful microorganisms efficiently may be prevented by the maintaining of the preservation fluid in the blood treatment unit, which allows extended use of the blood treatment unit. Typically, the maintaining of the preservation fluid in the blood treatment unit is achieved by filling the blood treatment unit with the preservation fluid and keeping the preservation fluid in the blood treatment unit until a next blood treatment session is prepared. An additional advantage lies in the possibility to use the treatment fluid concentrates already mounted on the blood treatment apparatus for the preservation, which is cost effective and keep labor hours down within busy dialysis clinics.

The blood treatment may further be configured to fill the blood line with the preservation fluid and maintain the preservation fluid in the blood line until the next blood treatment session is prepared. In preparation of the next blood treatment session the preservation fluid is then dispatched from the blood line. In some embodiments the blood treatment unit and the blood line are arranged as a common, disposable unit.

The blood treatment apparatus may also be configured to fill the fluid line with the preservation fluid and maintain the preservation fluid in the fluid line until the next blood treatment session is prepared. In preparation of the next blood treatment session the preservation fluid is dispatched from the fluid line.

The preservation fluid may have a pH value less than 4.5, less than 4.0, less than 3.0 or less than 2.0.

The preservation fluid may comprise an electrolyte solution or an electrolyte solution having a water activity of less than 0.97, less than 0.94, or less than 0.86.

The preservation fluid may comprise an acidic electrolyte solution, an acidic electrolyte solution having a pH value less than 4.5, an acidic electrolyte solution having a water activity of less than 0.97, an acidic electrolyte solution having a pH value less than 4.5 and having a water activity of less than 0.97, or an acidic electrolyte solution having any combination of above given ranges for pH and water activity.

In some embodiments the preservation fluid comprises at least one of hydrochloric acid, citric acid, acetic acid, N-acetylcystein, ascorbic acid, α-ketoglutarate, gluconic acid, or combinations thereof.

The preservation fluid may comprise an A-concentrate of a type that is used to prepare the treatment fluid. Such an A-concentrate may comprise an acid and electrolytes usually used to prepare a treatment fluid, except for bicarbonate.

The acid may be at least one of hydrochloric acid, citric acid, acetic acid, N-acetylcystein, ascorbic acid, α-ketoglutarate, gluconic acid, or combinations thereof.

The electrolytes may among others include at least one of sodium ions, calcium ions, potassium ions, magnesium ions and chloride ions, or combinations thereof.

This A-concentrate may be diluted to some extent, depending on the original concentrations of the component in the A-concentrate.

The preservation fluid may comprise only electrolytes, e.g. in form of sodium chloride. Such a preservation fluid may be provided from a two-part A-concentrate provided from two containers, where one container contains sodium chloride and the other container contains acid and optionally additional electrolytes. By using only the container comprising the sodium chloride, a preservation fluid having a water activity of less than 0.97 may be provided.

The blood treatment apparatus may be configured to maintain the preservation fluid in the blood treatment unit for at least 8 hours until the next blood treatment session is prepared.

The blood treatment apparatus may be configured to, prior filling the blood treatment unit with the preservation fluid, flush a rinsing fluid through the blood treatment unit.

The rinsing fluid may comprise treatment fluid, purified water, saline solution, or combinations thereof.

In some embodiments the blood treatment apparatus is configured to, prior filling the blood treatment unit with the preservation fluid, fill the blood treatment unit with a protein solvent, maintain the protein solvent in the blood treatment unit for a predetermined period of time, and dispatch the protein solvent from the blood treatment unit.

The blood treatment apparatus may be configured to, prior filling the blood treatment unit with the preservation fluid and after the dispatching the protein solvent, flush a rinsing fluid through the blood treatment unit.

Again, the rinsing fluid may comprise treatment fluid, purified water, saline solution, or combinations thereof.

The protein solvent may comprise a bicarbonate containing solution. In some embodiments the protein solvent comprises a bicarbonate containing dialysate concentrate of a type that is used to prepare the treatment fluid passed through the blood treatment unit during the blood treatment operation. Optionally the protein solvent consists of a bicarbonate containing dialysate concentrate of a type that is used to prepare the treatment fluid passed through the blood treatment unit during the blood treatment operation.

The blood treatment apparatus may further comprise a processing unit and processing instructions which when executed on the processing unit cause the blood treatment apparatus to fill the blood treatment unit with the preservation fluid and maintain the preservation fluid in the blood treatment unit until a next blood treatment session.

According to another aspect of the present invention a method is provided for a blood treatment apparatus that is adapted to preserve a blood treatment unit between blood treatment sessions. The blood treatment apparatus comprises the blood treatment unit, a blood line configured to pass blood through the blood treatment unit and deliver treated blood to a target vessel, and a fluid line configured to pass treatment fluid through the blood treatment unit and deliver used/spent treatment fluid to a drain. The method comprises performing a blood treatment session and thereby use of the blood treatment unit. Thereafter the blood treatment unit is filled with a preservation fluid that comprises at least one treatment fluid concentrate of a type that is used to prepare the treatment fluid, and the preservation fluid is maintained in the blood treatment unit until a next blood treatment session is prepared. In preparation of a next blood treatment session the preservation fluid is dispatched from the blood treatment unit. Finally the next blood treatment session is performed which thereby includes extended use of the blood treatment unit.

The method may be configured to implement any features discussed in connection with the blood treatment apparatus, and shares the corresponding advantages.

Still other objectives, features, aspects and advantages of the invention will become apparent from the following detailed description when taken in conjunction with the claims and drawings.

BRIEF DESCRIPTION OF THE DRAWINGS

Embodiments of the invention will now be described, by way of example, with reference to the accompanying schematic drawings, in which.

DETAILED DESCRIPTION OF THE INVENTION

FIG. 1

Figure 1:
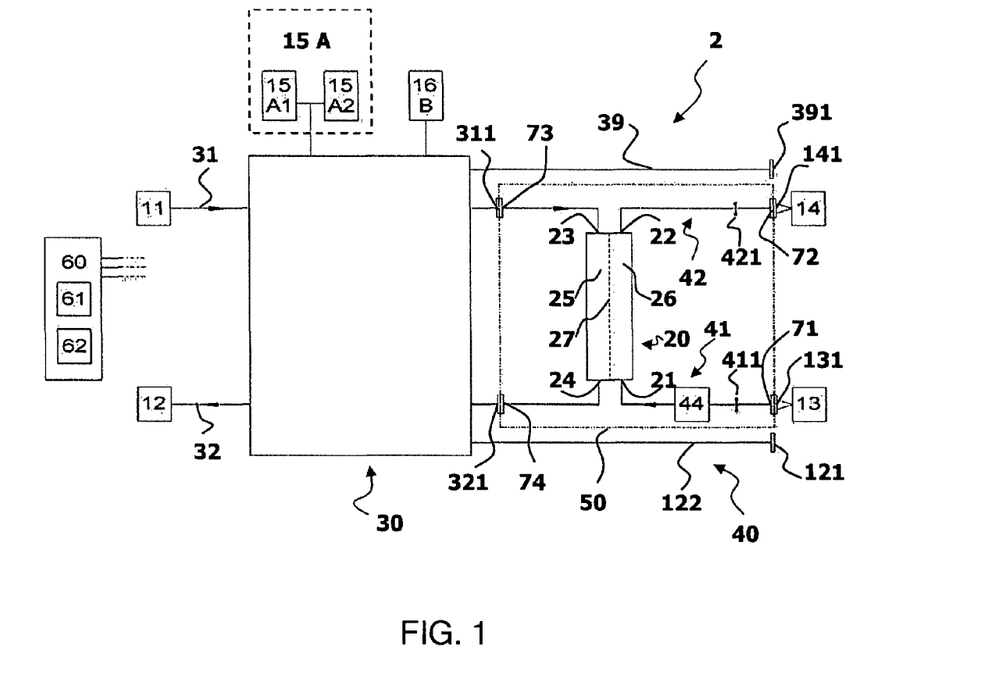
FIG. 1 illustrates a blood treatment apparatus arranged to perform a blood treatment session.

With reference to FIG. 1 an embodiment of a blood treatment apparatus 2 for extracorporeal blood treatment, such as dialysis, is illustrated. The blood treatment apparatus 2 (dialysis machine) comprises a blood treatment unit 20 and a blood line 40 with a blood pump 44 arranged to withdraw blood from a blood source 13, pass the blood through the blood treatment unit 20 (in which the blood is treated) and deliver the treated blood to a target vessel 14.

Within the blood treatment unit 20, a semi-permeable membrane 27 is present and divides the blood treatment unit 20 into a blood compartment 26 with a blood inlet 21 and a blood outlet 22, and a treatment fluid compartment 25 that has a fluid inlet 23 and a fluid outlet 24. The membrane 27 allows the treatment fluid to interact with the blood in a manner known within the art.

Blood Line

The blood line 40 is divided into an blood withdrawal line 41 and a blood return line 42. The blood withdrawal line 41 has a first connector device 71 that is connected to a first blood access device 131 in form of e.g. a needle arrangement or a catheter device that is inserted into the blood source 13. The blood return line 42 has a second connector device 72 that is connected to a second blood access device 141 in form of e.g. a needle arrangement or a catheter device that is inserted into the target vessel 14. The blood withdrawal line 41 thereby connects the blood source 13 to the blood inlet 21 of the blood treatment unit 20, while the blood return line 42 connects the blood outlet 22 of the blood treatment unit 20 with the target vessel 14.

Both the blood withdrawal line 41 and the blood return line 42 has clamping means 411, 421 (automatically and/or manually operated) allowing the blood withdrawal line 41 and the blood return line 42 to be repeatedly opened and closed, such that blood or some other fluid may be allowed respectively prevented to pass through the respective connector device 71, 72. The clamping means 411, 421 may be opened and closed by receiving control signals from a processor unit 60 of the blood treatment apparatus 2, such that a flow through the blood line 40 and blood compartment 26 may be controlled. The clamping means 411, 421 may also be integrated with respective connector device 71, 72 such that a disconnect action automatically closes the passage through respective connector device 71, 72.

For reasons of clarity of presentation, signal paths between the processor unit 60 and the components it controls have been omitted from the drawings.

The configuration of the blood line 40 and the blood treatment unit 20 may include various other components and control units generally present in blood treatment apparatuses. The blood source 13 and target vessel 14 may be a patient that receives blood treatment, but may also be bags of blood that are handled by operators. Even though the blood source 13 and the target vessel 14 are shown as separate units, they may be one and the same unit. The blood treatment apparatus 2 may be made to operate so as to perform single-needle dialysis and/or double-needle dialysis, and may therefore include some additional components conventionally used for this purpose.

Fluid Line

The blood treatment apparatus 2 has a fluid line 30 arranged to pass treatment fluid (fresh dialysis fluid) through the blood treatment unit 20 and deliver used/spent treatment fluid to a drain 12. The drain 12 may, for example, be a fluid sink, a sewer, a receptacle or any other component or discharge that may receive used/spent treatment fluid. The fluid line 30 is divided into an upstream fluid line 31 that connects a source of purified water 11 with the fluid inlet 23 of the blood treatment unit 20, and a downstream fluid line 32 that connects the fluid outlet 24 of the blood treatment unit 20 with the drain 12.

In the upstream fluid line 31 the treatment fluid is prepared from purified water 11, a so called A-concentrate, which may be contained in a container 15A connected to the upstream fluid line 31, and a so called B-concentrate, which may be contained in a container 16B connected to the upstream fluid line 31. The A-concentrate may be divided into two separate concentrates, as shown in FIG. 1, in container 15A1 and 15A2, but may also constitute a single A-concentrate in one container 15A. The mixing of the purified water and concentrates may be done according to conventional techniques and may include measuring conductivity of the partly prepared concentrates as well as of the treatment fluid, this may include sending conductivity measurement values to the processor unit 60 which in turn may control the mixing process such that a desired composition is obtained for the treatment fluid.

As will be explained below, the A-concentrate(s) and B-concentrate may be used for preparing the treatment fluid as well as for preserving the blood treatment unit 20.

The flow through the downstream fluid line 32 to the drain 12 may also be controlled by the processor unit 60.

The blood treatment unit 20 and the blood line 40 may be arranged as a common, disposable unit 50 in the form of a unitary device that may be disconnected from the blood treatment apparatus 2 and discarded once a blood treatment session of a patient is completed. When a new patient shall undertake treatment by the blood treatment apparatus 2, a new and similar common unit 50 is connected to the apparatus 2 and a treatment session may commence. For allowing the disposable unit 50 to be connected to the apparatus 2, a third connector device 73 is arranged in the upstream fluid line 31 and a fourth connector device 74 is arranged in the downstream fluid line 32.

The third and fourth connector devices 73, 74 are part of the disposable unit 50 or the blood treatment unit 20, and the third connector device 73 is connected to an upstream connector device 311. The fourth connector device 74 is connected to a downstream connector device 321. Alternatively or additionally, each of the third and fourth connector devices 73, 74 and the upstream and downstream connector devices 311, 321 may have clamping means (not shown) separated or integrated as disclosed above for the connector devices 71, 72, which may, manually or automatically, be opened and closed.

Concentrates

Typically, the A-concentrate in the container 15A or the containers 15A1 and 15A2 may be a concentrate, or concentrates containing acid and electrolytes usually used to prepare a treatment fluid, except sodium bicarbonate. The acid may be at least one of hydrochloric acid and organic acid, such as citric acid, acetic acid, N-acetylcystein, ascorbic acid, α-ketoglutarate, gluconic acid, etc or combinations thereof. The electrolytes may among others include at least one of sodium ions, calcium ions, potassium ions, magnesium ions, chloride ions, or combinations thereof.

The A-concentrate may further contain glucose or glucose-like compounds.

During a treatment session, the A-concentrate(s) is (are) mixed with purified water and contributes to the acidic component of the treatment fluid that is passed through the treatment unit 20 during the treatment session. The A-concentrate is highly acidic and may have a pH value of about 2 in its concentrated form. When diluted to the concentration used in preparation of the treatment fluid, the pH value may be less than 4.5. An example of commercially available A-concentrate contained in a container is a product named SoftPac™, which is provided by Gambro.

As disclosed above, the A-concentrate may also be provided from two containers, where one container contains sodium chloride (container 15A1) and the other container contains acid and optionally additional electrolytes which includes at least one of calcium ions, potassium ions, magnesium ions, chloride ions, or combinations thereof (container 15A2). Such a two-part A-concentrate system is provided by Gambro under the name of SelectBag® and SelectCart®. This allows for control of the concentration of sodium chloride in the treatment fluid independently from the acid and other optional electrolytes.

The B-concentrate in container 16B may comprise sodium bicarbonate, either as a concentrated solution or as a powder which may be dissolved by purified water on-line in the blood treatment apparatus 2 during the treatment session. The B-concentrate contributes to the basic and buffer component of the treatment fluid that is passed through the treatment unit 20 during the treatment session. Specifically, the B-concentrate may comprise, or may consist of, a sodium bicarbonate containing dialysate concentrate of a type that is used to prepare the treatment fluid that is passed through the blood treatment unit 20 during a blood treatment session. One example of a commercially available B-concentrate is the product named BiCart®, which is provided by Gambro.

The fluid line 30 may implement known techniques and standards, and may thus include various components and control units generally used in blood treatment apparatuses, such as filters, flow meters, pressure sensors, additional pumps, valves and clamps etc.

Preservation Fluid

The preservation fluid is a fluid intended to prevent growth of potentially harmful microorganisms between treatment sessions. It may be used in the blood treatment unit 20 and/or in the blood line 40. The preservation fluid may also be used to prevent growth of potentially harmful microorganisms in the fluid line 30 between treatment sessions.

The preservation fluid is prepared in the blood treatment apparatus 2 using available concentrates. Thus, the preservation fluid may comprise at least one treatment fluid concentrate of a type that is used to prepare the treatment fluid.

The preservation fluid may comprise an A-concentrate. As disclosed above in the section "Concentrates", such an A-concentrate may comprise acid and electrolytes usually used to prepare a treatment fluid, except for bicarbonate. Such an A-concentrate may be diluted by purified water within different ranges depending on the original concentrations of the components in the A-concentrate.

The preservation fluid may further comprise only electrolytes. Such a preservation fluid may be provided from a two-part A-concentrate as disclosed above under the section "Concentrates". By using only the container comprising sodium chloride, a preservation fluid only comprising electrolytes may be provided. By diluting such a sodium chloride concentrate, different degree of water activity, $a_w$, may be provided in the preservation fluid. Also here, a dilution may be applied, maintaining a relatively low water activity, $a_w$, below 0.97.

Further, having such a two-part A-concentrate also allows for the possibility to provide a preservation fluid by only using the part of the A-concentrate comprising acid and optional other electrolytes but for sodium chloride. A preservation fluid having an acidic pH, a pH value below 4.5, but not necessarily having a water activity less than 0.97 may then be provided. Also here different dilutions of the A-concentrate may be prepared to provide the preservation fluid, which then is mainly acidic.

Tests

Tests have shown that a preservation fluid based on a diluted A-concentrate efficiently may preserve a blood treatment unit, a blood line and/or a fluid line by preventing growth of harmful microorganisms.

Microorganisms require certain basic nutrients such as water, a source of energy, nitrogen, vitamins, and minerals for growth and maintenance of metabolic functions. The amount and type of nutrients required range widely depending on the type of microorganism. In order to prevent growth of microorganisms one may restrict one or several of the above mentioned requirements for growth. Moreover, temperature, pH and water activity will also affect growth and survival of the microorganisms.

Microorganisms need available water for growth. The amount of water needed for growth of microorganisms varies. The water requirement is expressed in terms of available water or water activity ($a_w$). The $a_w$ of purified water is 1.00. Low $a_w$ has traditionally been used to control microbial deterioration of food. Low water activity will also prevent microbial growth within pharmaceutical drug products.

Water activity may be combined with other preservation factors, such as temperature, high and low pH etc. to establish conditions that inhibit microorganisms. Different microbial inhibitory factors that might not prevent growth when considered singly prevent growth when used together.

Water activity is defined as the ratio of water vapour pressure of the product of interest to the vapour pressure of pure water at the same temperature, $a_w = P/P_0$ where P=vapour pressure of the solution and $P_0$=vapour pressure of pure water. The $a_w$ may be manipulated in products by a number of means, including addition of solutes such as salt or sugar, physical removal of water by drying, or binding of water to various macromolecules. An $a_w$ value stated for a microorganism is generally the minimum $a_w$ which supports growth. In table 1 water activities required to support the growth of representative microorganisms are presented. At $a_w$ values below the minimum for growth, the microorganisms do not necessarily die. The microorganisms may however remain dormant. The limiting value of water activity for the growth of any microorganism is about 0.6 (USP<1112>).

TABLE 1

Water Activities ($a_w$), measured at 25° C., required to support the growth of representative microorganisms (adapted from USP <1112>)

| Bacteria | Water activity (aw) | Molds and yeasts | Water activity (aw) |
| --- | --- | --- | --- |
| Pseudomonas aeruginosa | 0.97 | Saccharomyces cerevisiae | 0.90 |
| Bacillus cereus | 0.95 | Candida | 0.88 |
| Clostridium botulinum Type A | 0.95 | Aspergillus niger | 0.77 |
| Escherichia coli | 0.95 | Zygosachharomyces rouxii (osmophilic yeast) | 0.62 |
| Clostridium perfringens | 0.95 | | |
| Lactobacillus viridescens | 0.95 | | |
| Salmonella spp. | 0.95 | | |
| Enterobacter aerogenes | 0.94 | | |
| Bacillus subtilis | 0.90 | | |
| Micrococcus lysodekticus | 0.93 | | |

TABLE 1-continued

Water Activities ($a_w$), measured at 25° C.,
required to support the growth of representative
microorganisms (adapted from USP <1112>)

| Bacteria | Water activity (aw) | Molds and yeasts | Water activity (aw) |
|---|---|---|---|
| Staphylococcus aureus | 0.86 | | |
| Halobacterium halbium (halophilic bacterium) | 0.75 | | |

Sodium Chloride

The preserving effect of sodium chloride (NaCl) involves more than the dehydrating capacity. The minimum $a_w$ for the growth of various microorganisms is higher when NaCl is used compared to other solutes such as glycerol (Taormina, 2010). Please see table 2 below for water activity in various NaCl solutions.

TABLE 2

Water Activity of Various NaCl Solutions
(adapted from FDA Bad Bug Book)

| Percent NaCl (w/v) | Molal | Water Activity (aw) |
|---|---|---|
| 0.9 | 0.15 | 0.995 |
| 1.7 | 0.30 | 0.99 |
| 3.5 | 0.61 | 0.98 |
| 7.0 | 1.20 | 0.96 |
| 10.0 | 1.77 | 0.94 |
| 13.0 | 2.31 | 0.92 |
| 16.0 | 2.83 | 0.90 |
| 22.0 | 3.81 | 0.86 | pH

In general, most microorganisms grow best in an environment with a pH range between 6-8, yeasts 4.5-6.0 and filamentous fungi 3.5-4.0. The ability of low pH to restrict microbial growth has been used since the earliest times in the preservation of foods with acetic and lactic acids. The activity and stability of macromolecules such as enzymes are greatly affected by the acidity or alkalinity of the environment.

The ability of microorganisms to grow or survive in acidic environments depends on the proton concentration which is determined by the pH, and on the type of acid. It is well known that although addition of strong acids has a more profound effect on pH they are less inhibitory than several weak organic acids at the same pH. The inhibitory properties of many of the organic acids, acetic, benzoic, citric, lactic, proprionic, and sorbic acids make them widely used as preservatives. Organic acids are more effective as preservatives in the non-dissociated state. In the non-dissociated states weak acid molecules pass through the membrane. Inside the cell the acid dissociates and hence lowers the pH of the cytoplasm. The cell will try to maintain its internal pH by neutralizing or by active transport of the protons out from the cell. In doing so the cell waste energy from growth related functions which hinder the growth. If the pH of the environment is sufficiently low and the extracellular concentration of the acid high the cell will eventually die.

Growth studies of the bacteria Staphylococcus, Serratia, and Bacillus showed that they could not increase in acidic (pH 5.6 or lower) total parenteral solutions without lipids whereas the yeast Candida albicans grew at pH 5.5 (Kuwahara et al., 2010). Moreover growth studies with the yeast C. albicans adding different weak acids to the medium resulting in pH in the range 2.3 to 3.6 (acetic acid pH 3.6; citric acid pH 2.4, succinic acid pH 2.8, tartaric acid pH 2.3) showed that the C. albicans grew as well as the control with pH 5.5 in media (De Seta et al., 2009). However adding fumaric and maleic acid resulting in pH 2.6 and 2.0, respectively, resulted in inhibition of growth.

TABLE 3

Approximate pH values permitting growth
(adapted from FDA, Food)

| Microorganism | Minimum | Optimum | Maximum |
|---|---|---|---|
| Bacillus cereus | 4.9 | 6.0-7.0 | 8.8 |
| Clostridium botulinum | 4.6 | | 8.5 |
| Escherichia coli | 4.4 | 6.0-7.0 | 9.0 |
| Clostridium perfringens | 5.5-5.8 | 7.2 | 8.0-9.0 |
| Salmonella spp. | 4.2 | 7.0-7.5 | 9.5 |
| Staphylococcus aureus | 4.0 | 6.0-7.0 | 10.0 |

REFERENCES

United States Pharmacopoeia (USP) chapter <1112> Application of water activity determination to non-sterile pharmaceutical products.

Food and Drug Administration (FDA) Bad Bug Book: Foodborne pathogenic microorganisms and natural toxins handbook. Factor affecting the growth of microorganisms in foods.

Taormina P. J. Implications of salt and sodium reduction on microbial food safety. Critical Reviews in food science and nutrition 50:209-227, 2010

Food and Drug Administration (FDA) Food chapter 3. Factors that influence microbial growth. Dec. 31, 2001.

Kuwahara T, Kaneda S, Shimono K, Inoue Y. Growth of microorganisms in total parenteral nutrition solutions without lipid. International Journal of medical Sciences 7(1):43-47, 2010

De Seta F, Schmidt M, Vu B, Essman M, Larsen B. Antifungal mechanisms supporting boric acid therapy of Candida vaginitis. Journal of Antimicrobial Chemotherapy 63:325-336, 2009

Test 1

A test 1 A-concentrate was used comprising: 210.7 g sodium chloride; 5.22 g potassium chloride; 7.12 g magnesium chloride; 9.01 g calcium chloride; 35 g glucose; 6.75 g citric acid, and purified water to a final volume of 1 liter.

This test 1 A-concentrate was then diluted with purified water to obtain test 1 diluted concentrates with the following proportions (test 1 A-concentrate:water): 1:1; 1:2; 1:4; 1:8; 1:16; 1:35.

pH and water activity was measured for each test 1 diluted concentrate, see table 4 below.

TABLE 4 pH and water activity measurements of test
1 diluted concentrates.

| Dilution | pH | Water activity $a_w$ |
|---|---|---|
| 1:1 | 1.4 | 0.86 |
| 1:2 | 2.0 | 0.94 |
| 1:4 | 2.3 | 0.97 |

TABLE 4-continued pH and water activity measurements of test
1 diluted concentrates.

| Dilution | pH | Water activity $a_w$ |
|---|---|---|
| 1:8 | 2.6 | 0.98 |
| 1:16 | 2.9 | 0.99 |
| 1:35 | 3.2 | 1.0 |

The water activity was measured in the different dilutions with AQUA Lab 4TEV instrument from Decagon Devices at 25° C. according to the instructions from the manufacturer.

Figure 6:
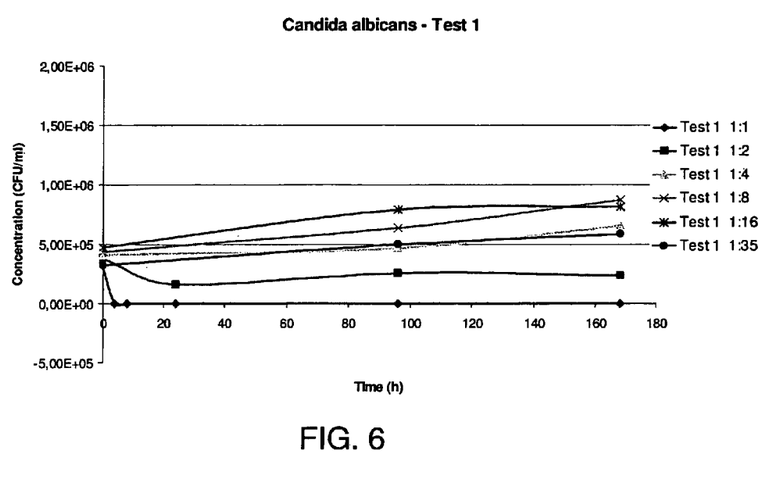

The test 1 diluted concentrates were then tested on yeast organism Candida albicans ATCC (American Type Culture Collection) 10231 and on the organism *Pseudomonas aeruginosa* ATCC 15442. The tests were performed by covering the respective organism with the different test 1 diluted concentrates, and the concentration of the organisms (Colony Forming Units (CFU) per ml) were measured over time. As may be seen from FIG. 6, the different test 1 diluted concentrates efficiently prevented growth of or killed (the 1:1 and 1:2 concentrates) the organism Candida albicans.

Figure 7:
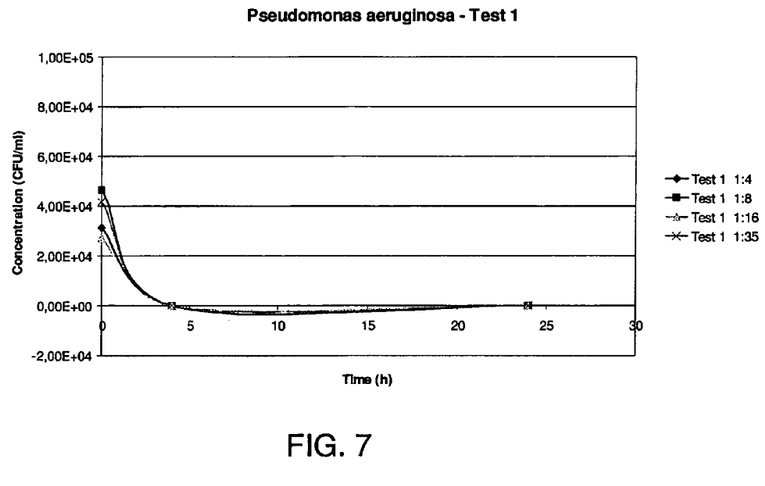

As may be seen from FIG. 7, the different test 1 diluted concentrates were able to efficiently kill the organism *Pseudomonas aeruginosa*.

Test 2

A test 2 A-concentrate was used comprising: 210.7 g sodium chloride; 5.22 g potassium chloride; 7.12 g magnesium chloride; 9.01 g calcium chloride; 6.31 g acetic acid; and purified water to a final volume of 1 liter.

The test 2 A-concentrate was then diluted with purified water to obtain test 2 diluted concentrates with the following proportions (test 2 A-concentrate:purified water): 1:1; 1:2; 1:4; 1:8; 1:16; 1:35.

pH and water activity was measured for each test 2 diluted concentrate, see table 5 below.

TABLE 5 pH and water activity measurements of test
2 diluted concentrates.

| Dilution | pH | Water activity $a_w$ |
|---|---|---|
| 1:1 | 2.1 | 0.84 |
| 1:2 | 2.6 | 0.93 |
| 1:4 | 2.9 | 0.97 |
| 1:8 | 3.1 | 0.98 |
| 1:16 | 3.4 | 0.99 |
| 1:35 | 3.6 | 0.99 |

The test 2 diluted concentrates were then tested on the same organisms as the test 1 diluted concentrates above, by using the same method.

Figure 8:
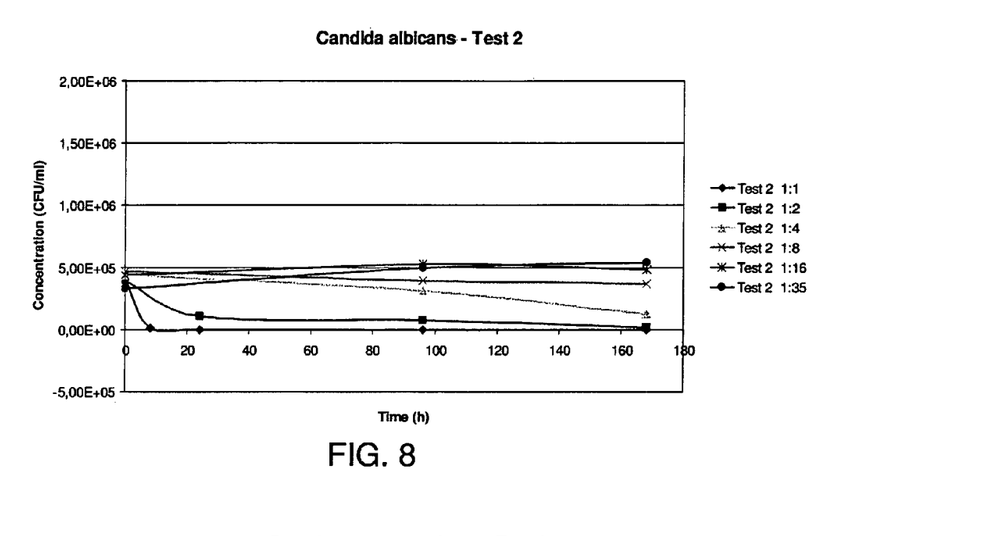

As may be seen from FIG. 8, the different test 2 diluted concentrates efficiently prevented growth of or killed (the 1:1, 1:2, 1:4, 1:8 second type diluted concentrates) the organism Candida albicans.

Figure 9:
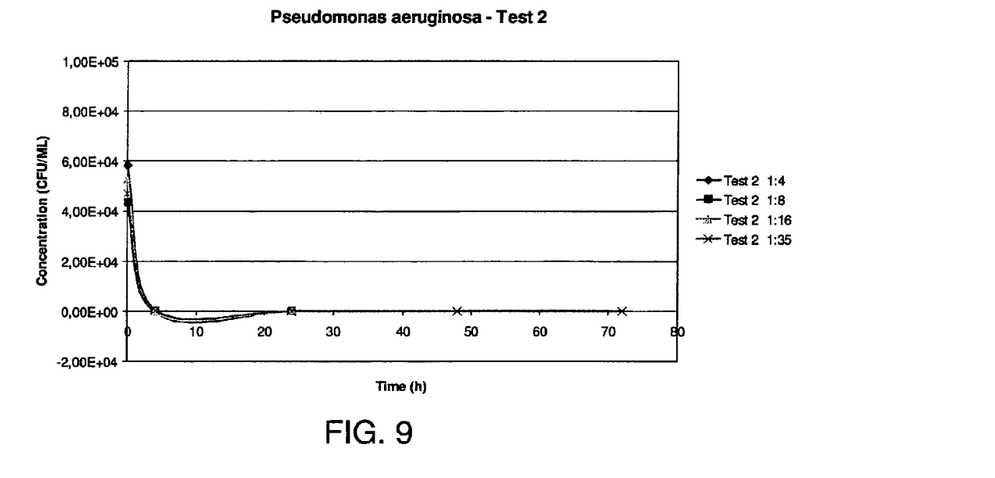

As may be seen from FIG. 9, the test 2 diluted concentrates were able to efficiently kill the organism *Pseudomonas aeruginosa*.

Preservation

The blood treatment apparatus 2 is configured to preserve the blood treatment unit 20 between blood treatment sessions such that it may be used an extended number of times. This preservation may also include the blood line 40 such that the disposable unit 50 may be preserved. In addition to preserving the blood treatment unit 20 and optionally also the blood line 40, the fluid line 30 may also be preserved.

For implementing the preservation the blood treatment apparatus 2 has a fluid branch line 39 that is connected between the upstream fluid line 31 and a first preservation connector 391. The first preservation connector 391 may be opened respectively closed, either manually or by receiving control signals from the processor unit 60, and is connectable to the first connector device 71 of the blood withdrawal line 41 (or alternatively to the second connector device 72 of the blood return line 42).

The exemplified blood treatment apparatus 2 may also have a discharge line 122 that is arranged in between the drain 12 and a second preservation connector 121. The second preservation connector 121 may also be opened respectively closed, either manually or automatically, e.g. by receiving control signals from the processor unit 60, and is connectable to the second connector device 72 of the blood return line 42 (or alternatively to the first connector device 71 of the blood withdrawal line 41).

FIG. 2

Figure 2:
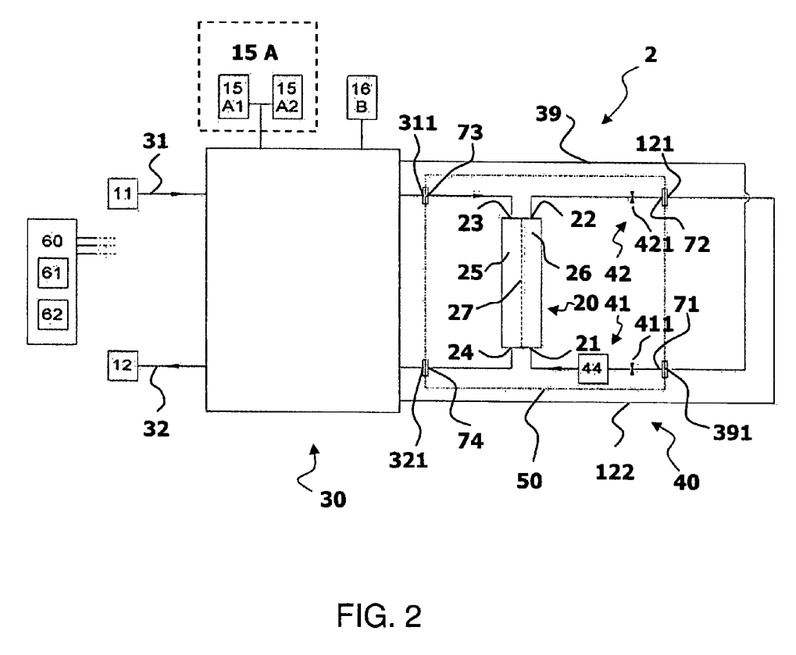
FIG. 2 illustrates the blood treatment apparatus of FIG. 1 when it is arranged to preserve a blood treatment unit.

With reference to FIG. 2 the blood treatment apparatus 2 is illustrated when it is arranged to preserve the blood treatment unit 20, the blood line 40 and/or the fluid line 30. As may be seen, the blood access devices 131, 141 are now disconnected from the blood line 40. Instead, the first connector device 71 is connected to the first preservation connector 391 and the second connector device 72 is connected to the second preservation connector 121. The upstream fluid line 31 may then direct a flow of preservation fluid into the blood line 40.

When the change from the blood access devices 131, 141 to the preservation connectors 391, 121 is performed, the blood withdrawal line 41 and the blood return line 42 may be clamped by clamping means 411, 421.

When the blood treatment apparatus 2 is arranged to preserve the fluid line 30, the upstream fluid line 31 may then direct a flow of preservation fluid through the fluid line 30 in the same route as the treatment fluid normally flows during a treatment session.

When both the fluid line 30 and the blood treatment unit 20 and the blood line 40 is to be preserved, the upstream fluid line 31 may direct a flow of preservation fluid through both the fluid line 30 and the blood line 40, or one before the other.

FIG. 3

Figure 3:
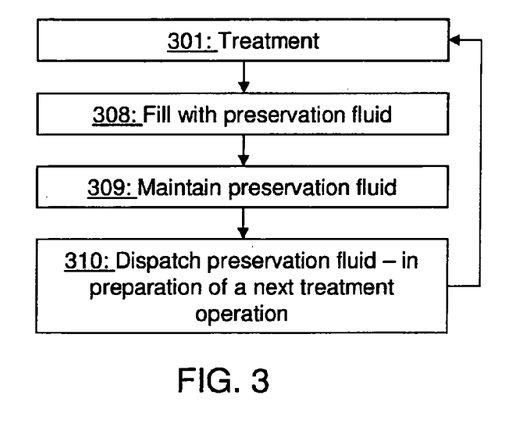
FIG. 3 is a flow chart of a general method for preserving a blood treatment unit, as performed by the blood treatment apparatus of FIG. 2.

With further reference to FIG. 3, when the blood treatment apparatus 2 is arranged as in FIG. 2 it may preserve the blood treatment unit 20 by performing a number of steps.

The preservation presumes that a first step 301 of the method includes preparation (priming) of the blood treatment apparatus 2 and the following blood treatment session for a patient, which may be performed according to known techniques and which results in that the blood treatment unit 20 is used.

During the blood treatment session no fluid may enter or exit the fluid branch line 39, and A-concentrate(s) and B-concentrate are continuously used for preparing the treatment fluid that is passed through the blood treatment unit 20.

The first and second connector devices 71, 72 are sealed, as disclosed above, at the end of the first step 301 such that no fluid may flow from or to the blood source 13 and the target vessel 14, respectively. The first and second blood access devices 131 and 141 are then disconnected from the blood line 40 and the first and second connector devices 71, 72 are connected to the preservation connectors 391, 121.

In a next step 308 the blood treatment unit 20 is filled with preservation fluid. In this step the processor unit 60 may control the dilution and mixing such that the concentration of the A-concentrate in the treatment fluid is increased in comparison with the concentrate level that is used for the treatment fluid, while there is no supply of the B-concentrate into the upstream fluid line 31. The preservation fluid is fed to the blood treatment unit 20 via the fluid branch line 39 into the connector devices 71, 72 and the preservation connectors 391, 121. The processor unit 60 may be responsible for controlling the connector devices 71, 72, the preservation connectors 391, 121 such that the preservation fluid may be fed from the upstream fluid line 31, through the fluid branch line 39 to the blood withdrawal line 41.

The filling of the blood treatment unit 20 may be stopped when the blood line 40 and the blood compartment 40 is filled with preservation fluid. The filling operation is completed by closing the connector devices 71, 72 and/or the preservation connectors 391, 121. The effect of the filling is that both the blood treatment unit 20 and the blood line 40 are filled with the preservation fluid. When preservation fluid is fed into the blood line 40 any fluid already present in the blood line 40 is rinsed out and is conveyed to the drain 12. Of course, it is possible to use a separate drain for fluid that is rinsed out, which may be desirable when the rinsed out fluid comprises blood or blood residues.

In a next step 309 the preservation fluid is maintained in the blood treatment unit 20 until a next blood treatment session is prepared. This means that the connector devices 71, 72 and/or the preservation connectors 391, 121 remain closed until the preparations for the next blood treatment session commence. Typically, when treating an average patient the preservation fluid is maintained in the blood treatment unit 20 for 8 hours or longer, such as 16-22 hours or even up to 70 hours or more. The result of this step is that harmful microorganism growth in the blood treatment unit 20 or in the blood line 40 is prevented.

In a next step 310 the preservation fluid is dispatched from the blood treatment unit 20 and the blood line 40. This is done as part of preparing the blood treatment apparatus 2 for a next blood treatment session and may be accomplished by opening the connector devices 71, 72 and the preservation connectors 391, 121. Purified water is then fed from the source of purified water 11, into the fluid branch line 39, into the blood withdrawal line 41, into the blood treatment unit 20, out of the blood return line 42, through the discharge line 122, and to the drain 12. The discharge line 122 may be in fluid communication with the downstream fluid line 32, but may also be directly connected to drain (not shown). When the preservation fluid is dispatched a new treatment operation may start, i.e. the method may be re-iterated by returning to the first step 301.

FIG. 4

The method described in connection with FIG. 3 is a general description of how the blood treatment apparatus 2 may preserve the blood treatment unit 20. A number of additional steps for preservation may be performed, as illustrated with reference to the more detailed method of FIG. 4.

Figure 4:
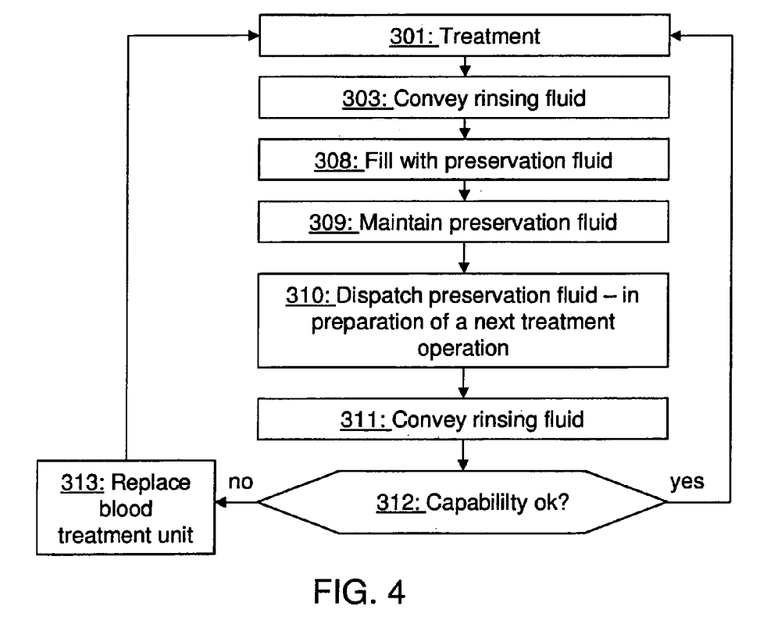
FIG. 4 is a flow chart of a more detailed embodiment of the method of FIG. 3.

In a first step 301 of the detailed method, a blood treatment session is performed for a patient as described in connection with FIG. 3. As mentioned, this results in that the blood treatment unit 20 is used and in that both A-concentrate and B-concentrate are continuously used for preparing the treatment fluid that is passed through the blood treatment unit 20.

In a next step 303 the blood treatment unit 20 is rinsed or flushed. This may be accomplished by conveying a rinsing fluid from the upstream fluid line, into the fluid branch line 39, into the blood withdrawal line 41, through the blood treatment unit 20, out of the blood return line 42, through the discharge line 122, and to the drain 12. By virtue of the blood lines' connection to the blood treatment unit 20, the blood line 40 is also rinsed when the blood treatment unit 20 is rinsed. The rinsing typically removes blood residues from the blood treatment unit 20 and the blood line 40. The rinsing fluid may be purified water, but may also comprise treatment fluid or a physiological saline solution.

In three next steps 308, 309, 310 the blood treatment unit 20 and blood line 40 are filled with the preservation fluid, the preservation fluid is maintained therein and is thereafter dispatched, just as described in connection with steps 308, 309, 310 of FIG. 3.

In a next step 311 rinsing of the blood treatment unit 20 and the blood line 40 is performed again, which may be done in a manner corresponding to step 303. The step 311 of rinsing typically removes any residues of preservation fluid, and may be an integral part of the step 310 of dispatching of the preservation fluid. The rinsing fluid may initially be purified water, but may at the end of the rinsing operation comprise treatment fluid or at least a physiological saline solution.

When the preservation fluid is rinsed out a new treatment operation may start, i.e. the method may be re-iterated by returning to the first step 301.

However, before returning to step 301 a step of checking the blood treatment unit 20 for its capability to treat blood may be performed. This may be done by performing a so-called conductivity measurement where a conductivity pulse is created at the fluid inlet 23 of the blood treatment unit 20 and a step response is measured by means of e.g. a conductivity cell (not shown) arranged downstream the blood treatment unit 20. A so called clearance, i.e. indication of the current performance of the blood treatment unit 20, may thereafter be calculated by the processor unit 60 based on the step response.

If the clearance is insufficient a next step 313 of replacing the blood treatment unit 20 with a new similar one is performed, and thereafter the first step 301 of performing a blood treatment session may be reentered. On the other hand, if the clearance is sufficient, step 301 is reentered but without replacing the blood treatment unit 20.

It is possible to perform the step 312 of checking the capability of the blood treatment unit 20 during the blood treatment session, i.e. steps 301 and 312 may be performed in parallel instead of sequentially. Alternatively, the step 312 of checking the blood treatment unit 20 for its capability for treating the blood may be done directly after step 301, before step 303 where the blood treatment unit 20 is rinsed. In either case, if the capability of the blood treatment unit is insufficient then step 313 of replacing the blood treatment unit 20 may be entered directly after step 301 is complete.

During the step 301 of performing the blood treatment session, or during any other subsequent step, an integrity test may be done for ensuring that the membrane 27 in the blood treatment unit 20 does not leak. If the integrity test should show that the membrane 27 leaks, then the step 313 of replacing the blood treatment unit 20 should be entered. The integrity test may be embodied as an integral part of the step 312 of checking the capability of the blood treatment unit 20.

To verify that the blood line 40 is filled with a proper composition of preservation fluid or protein solvent, or that the blood line 40 is sufficiently rinsed during the steps of rinsing, the apparatus 2 may comprise conductivity meter (not shown) that is arranged in the discharge line 122. The conductivity meter may measure a composition of a fluid in the discharge line 122 and send a corresponding signal to the processor unit 60. The processor unit 60 may also or alternatively control the composition of the fluid that is fed into the fluid branch line 39, such that a proper fluid composition is fed into the blood line 40.

FIG. 5

Figure 5:
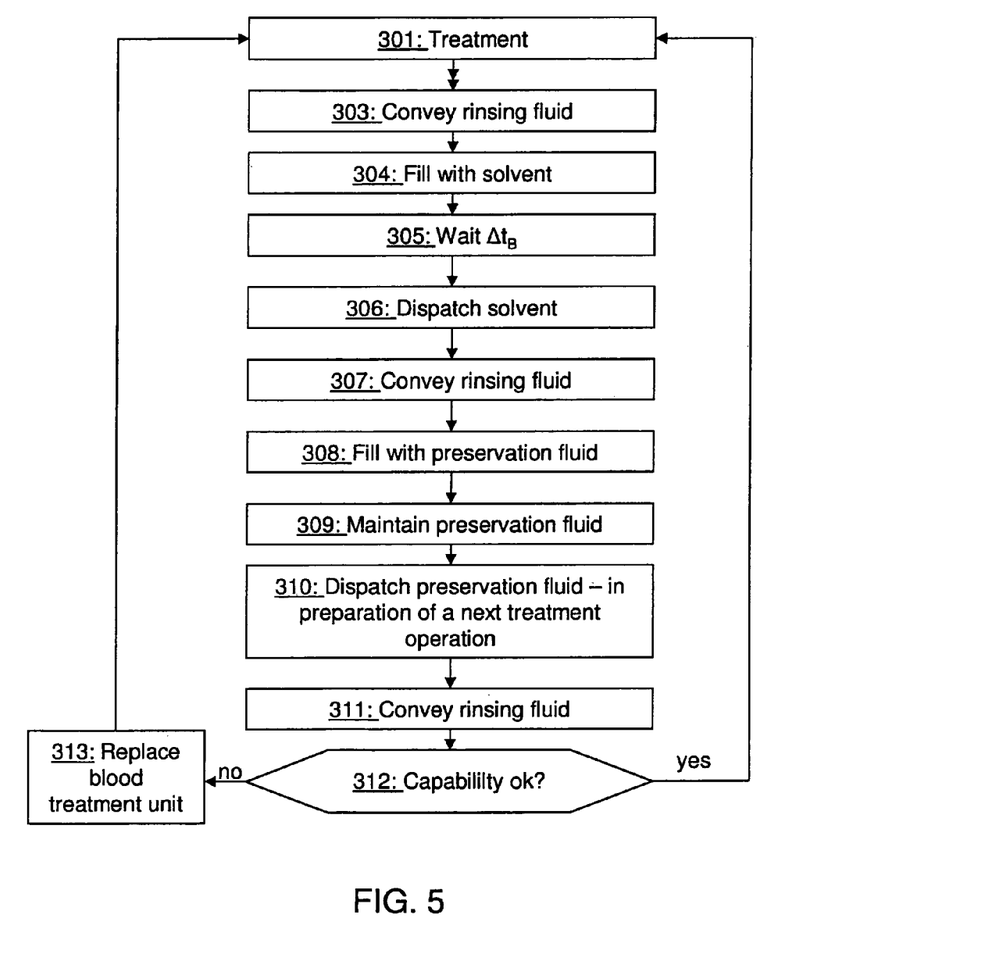
FIG. 5 is a flow chart of another embodiment of the method of FIGS. 3 and 4, and FIGS. 6-9 illustrate results of tests performed for evaluating preservation of a blood treatment unit.

The method described in connection with FIGS. 3 and 4 may comprise a number of additional steps for preservation, as illustrated with reference to the more detailed method of FIG. 5.

In a first step 301 of the detailed method, a blood treatment session is performed for a patient as described in connection with FIG. 3. As mentioned, this results in that the blood treatment unit 20 is used and in that both A-concentrate and B-concentrate are continuously used for preparing the treatment fluid that is passed through the blood treatment unit 20.

In a next step 303 the blood treatment unit 20 is rinsed or flushed as described in connection with FIG. 4.

In a next step 304 the blood treatment unit 20 and the blood line 40 are filled with a protein solvent like the B-concentrate described above. This step may be performed in a manner similar with step 308 of FIG. 3, with the difference that the processor unit 60 controls the dilution and mixing such that the concentration of the B-concentrate in the protein solvent is increased in comparison with the concentrate level that is used for the treatment fluid, while there is no supply of the A-concentrate into the upstream fluid line 31.

In a next step 305 the protein solvent is maintained in the blood treatment unit 20 for a predetermined period of time, $t\Delta_B$, such as 10-15 minutes. The result of this step is that blood proteins remaining in the blood treatment unit 20 and the blood line 40 are solved, which is accomplished by the protein solving characteristics of the B-concentrate (bicarbonate).

In a next step 306 the protein solvent is dispatched or flushed out from the blood treatment unit 20. Dispatching the protein solvent may be done in a manner corresponding to the dispatching of the preservation fluid in step 310 of FIG. 3.

In a next step 307 rinsing of the blood treatment unit 20 and the blood line 40 is performed again, which may be done in a manner corresponding to step 303. In this context, dispatching a fluid (in the form blood or any other solution) from the blood treatment unit 20 and the blood line 40 may in some embodiments result in rinsing or flushing. In a corresponding manner rinsing or flushing may result in dispatching a fluid in the blood treatment unit 20 and blood line 40. Thus, steps 306 and 307 may be integrated into one step. The rinsing typically removes the protein solvent together with any therein solved proteins.

In three next steps 308, 309, 310 the blood treatment unit 20 and blood line 40 are filled with the preservation fluid, the preservation fluid is maintained therein and is thereafter dispatched, just as described in connection with steps 308, 309, 310 of FIG. 3.

In two next steps 311 and 312 the blood treatment unit 20 and blood line 40 are rinsed again, and check of performance is done, just as described in connection with step 311 and step 312 of FIG. 4.

Preserve Fluid Line

In addition to as an alternative to preserving the blood treatment unit 20 and optionally the blood line 40, the fluid line 30 may be preserved in a similar manner. This may include filling the fluid line 30 with a preservation fluid like the one used for the blood treatment unit 20, and maintaining the preservation fluid in the fluid line 30 for e.g. the same period of time as maintaining the preservation fluid in the blood treatment unit 20.

Typically, the fluid line 30 is then filled with preservation fluid before, after or simultaneously to the blood treatment unit 20 is filled with preservation fluid. The preservation fluid may be discarded from the fluid line 30 before a next treatment operation by rinsing it with new treatment fluid.

Preserving the fluid line 30 may be done independently of the preserving of the blood treatment unit 20, i.e. the blood treatment apparatus 2 may be configured to: i) perform a blood treatment session and thereby use the fluid line 30, ii) fill the fluid line 30 with a preservation fluid comprising at least one treatment fluid concentrate of a type that is used to prepare the treatment fluid, iii) maintain the preservation fluid in the fluid line 30 until a next blood treatment session is prepared, iv) dispatch the preservation fluid from the fluid line 30 in preparation of a next blood treatment session, and v) perform a next blood treatment session and thereby use the fluid line 30 again.

Steps of the preservation method may be performed by the processor unit 60 that controls various parts of the blood treatment apparatus 2. For this purpose the processor unit 60 typically includes one or more processing devices such that a central processing unit 61 which may execute software instructions, i.e. computer program code that carry out relevant steps and operations described above. For this purpose the blood treatment apparatus 2 may include a computer-readable memory 62 that stores the software instructions. These may for development convenience be written in a high-level programming language such as Java, C, and/or C++ but also in other programming languages, such as, but not limited to, interpreted languages.

The steps of rinsing 303, 307, 311, filling 304, 308 and dispatching 306, 310 may be initiated by commands implemented by one or more software instructions stored on the computer-readable memory 62. Also, relevant controlled means for performing the method are typically controlled by the processor unit 60. From this follows, that the blood treatment unit is specifically configured to perform the described operations.

From a hardware perspective it may be said that the blood treatment unit comprises e.g. a pump capable of filling the blood treatment unit with the preservation fluid, and closure devices, for example in form of clamps, connector devices or valves, that maintain the preservation fluid in the blood treatment unit until a next blood treatment session is prepared. The pump may then dispatch the preservation fluid from the blood treatment unit in preparation of a next blood treatment session, and the apparatus may thereafter perform a next blood treatment session and thereby reuse the blood treatment unit.

Of course, the principles described herein for preserving a blood treatment unit may be employed in connection with other apparatuses as well, for example by apparatuses to which a blood treatment unit may be connected, filled with fluid and subsequently emptied from fluid. Moreover, if the connector devices 71-74 are closed after the blood treatment unit 20 is filled with preservation fluid, then the disposable unit 50 may be removed from the apparatus 2 and stored at some other suitable location until it shall be reused. In the meantime, the apparatus 2 may be used by another patient.

Also, other techniques for filling the blood treatment unit and maintaining a fluid therein may be used, and some method steps described herein may be performed in a different order than the illustrated one or may be combined, such as a dispatching step and its following rinsing step. Thus, although various embodiments of the invention have been described and shown, the invention is not restricted thereto, but may also be embodied in other ways within the scope of the subject-matter defined in the following claims.

The invention claimed is:

1. A blood treatment apparatus adapted to preserve a blood treatment unit between blood treatment sessions, the blood treatment apparatus comprising:
    the blood treatment unit;
    a blood line configured to pass blood through the blood treatment unit and deliver treated blood to a target vessel;
    a fluid line configured to pass treatment fluid through the blood treatment unit and,
    a processor configured to cause the blood treatment apparatus to:
    perform a blood treatment session during which the blood treatment unit is used to treat blood,
    fill the blood treatment unit with a preservation fluid comprising at least one treatment fluid concentrate of a type that is used to prepare the treatment fluid, the at least one treatment fluid concentrate comprising sodium chloride and at least one of hydrochloric acid, citric acid, acetic acid, N-acetylcysteine, ascorbic acid, ketoglutarate and gluconic acid, and having a pH value less than 4.5,
    maintain the preservation fluid in the blood treatment unit until a next blood treatment session is prepared,
    dispatch the preservation fluid from the blood treatment unit and rinse the blood treatment unit with the treatment fluid in preparation of a next blood treatment session, and
    perform a next blood treatment session using the blood treatment unit to treat blood.

2. A blood treatment apparatus according to claim 1, wherein the processor is configured to cause the blood treatment apparatus to fill the blood line with the preservation fluid, maintain the preservation fluid in the blood line until the next blood treatment session is prepared, and dispatch the preservation fluid from the blood line in preparation of the next blood treatment session.

3. A blood treatment apparatus according to claim 1, wherein the processor is configured to cause the blood treatment apparatus to fill the fluid line with the preservation fluid, maintain the preservation fluid in the fluid line until the next blood treatment session is prepared, and dispatch the preservation fluid from the fluid line in preparation of the next blood treatment session.

4. A blood treatment apparatus according to claim 1, wherein the preservation fluid comprises an electrolyte solution.

5. A blood treatment apparatus according to claim 4, wherein the preservation fluid comprises an electrolyte solution having a water activity of less than 0.97.

6. A blood treatment apparatus according to claim 1, wherein the processor is configured to cause the blood treatment apparatus to maintain the preservation fluid in the blood treatment unit for at least 8 hours until the next blood treatment session is prepared.

7. A blood treatment apparatus according to claim 1, wherein the blood treatment unit and the blood line are arranged as a common, disposable unit.

8. A blood treatment apparatus according to claim 1, configured to, prior filling the blood treatment unit with the preservation fluid, flush a rinsing fluid through the blood treatment unit.

9. A blood treatment apparatus according to claim 1, wherein the processor comprises a processing unit and processing instructions which when executed on the processing unit cause the blood treatment apparatus to fill the blood treatment unit with the preservation fluid and maintain the preservation fluid in the blood treatment unit until a next blood treatment session.

10. The blood treatment apparatus according to claim 1, wherein the at least one treatment fluid concentrate contains an electrolyte including ions selected from the group consisting of sodium ions, calcium ions, potassium ions, magnesium ions, chloride ions, and combinations thereof.

11. A method for a blood treatment apparatus adapted to preserve a blood treatment unit between blood treatment sessions, the blood treatment apparatus comprising the blood treatment unit, a blood line configured to pass blood through the blood treatment unit and deliver treated blood to a target vessel, and a fluid line configured to pass treatment fluid through the blood treatment unit and deliver used treatment fluid to a drain, the method comprising:
    performing a blood treatment session during which the treatment fluid flows through the blood treatment unit,
    filling the blood treatment unit with a preservation fluid including at least one treatment fluid concentrate of a type used to prepare the treatment fluid, the at least one treatment fluid concentrate comprising sodium chloride and at least one of hydrochloric acid, citric acid, acetic acid, N-acetylcysteine, ascorbic acid, ketoglutarate and gluconic acid, and having a pH value less than 4.5,
    maintaining the preservation fluid in the blood treatment unit until a next blood treatment session is prepared,
    discharging the preservation fluid from the blood treatment unit and rinse the blood treatment unit with the treatment fluid in preparation of a next blood treatment session, and
    performing a next blood treatment session using the blood treatment unit.

12. The method according to claim 11, wherein the at least one treatment fluid concentrate contains an electrolyte including ions selected from the group consisting of sodium ions, calcium ions, potassium ions, magnesium ions, chloride ions, and combinations thereof.

13. A method to treat blood during successive blood treatment sessions comprising:
    generating a blood treatment fluid from a treatment fluid concentrate;
    during a first blood treatment session, passing blood through a blood treatment unit and infusing the blood into a target vessel, while simultaneously passing the blood treatment fluid through the blood treatment unit,
    after the first blood treatment session, at least partially filling the blood treatment unit with a preservation fluid including a concentrate the same as or similar to the treatment fluid concentrate, the concentrate comprising sodium chloride and at least one of hydrochloric acid, citric acid, acetic acid, N-acetylcysteine, ascorbic acid, ketoglutarate and gluconic acid, and having a pH value less than 4.5;
    discharging the preservation fluid from the blood treatment unit and rinsing the blood treatment unit with the blood treatment fluid during preparation for the blood treatment unit from a next blood treatment session, and during the next blood treatment session, passing blood through a blood treatment unit and infusing the blood into a target vessel, while simultaneously passing the blood treatment fluid through the blood treatment unit.

14. The method of claim 13, wherein the step of at least partially filling is performed promptly after completion of the first treatment session.

15. The method of claim 13 wherein the step of at least partially filling includes filling a blood passage in the blood treatment unit with the preservation fluid.

16. The method according to claim 13, wherein the concentrate contains an electrolyte including ions selected from the group consisting of sodium ions, calcium ions, potassium ions, magnesium ions, chloride ions, and combinations thereof.

17. A blood treatment apparatus comprising:
a blood treatment unit,
a blood line coupled to the blood treatment unit, a blood source and to a target vessel, wherein the blood line and blood treatment unit form a blood passage between the blood source and the target vessel during a treatment session;
a fluid line coupled to the blood treatment unit, a treatment fluid source and a drain, wherein the fluid line and blood treatment unit form a fluid passage for the treatment fluid to flow from the treatment fluid source through the blood treatment unit and to the drain,
wherein the blood treatment unit has first and second operating modes and a preservation mode:
wherein during the first and second operating modes the blood treatment unit forms passages for blood and the blood treatment fluid during successive blood treatment sessions, and
during the preservation mode the blood treatment unit is filled with a preservation fluid comprising at least one treatment fluid concentrate of a type used to prepare the treatment fluid and the blood treatment unit is rinsed with the treatment fluid, the at least one treatment fluid concentrate comprising sodium chloride and at least one of hydrochloric acid, citric acid, acetic acid, N-acetylcysteine, ascorbic acid, ketoglutarate and gluconic acid, and having a pH value less than 4.5, and the preservation mode occurs between the first and second operating modes.

18. The blood treatment apparatus according to claim 17, wherein the at least one treatment fluid concentrate contains an electrolyte including ions selected from the group consisting of sodium ions, calcium ions, potassium ions, magnesium ions, chloride ions, and combinations thereof.

* * * * *